(12) United States Patent
Benvegnu et al.

(10) Patent No.: US 7,768,659 B2
(45) Date of Patent: Aug. 3, 2010

(54) DETERMINING COPPER CONCENTRATION IN SPECTRA

(75) Inventors: Dominic J. Benvegnu, La Honda, CA (US); Jeffrey Drue David, San Jose, CA (US); Boguslaw A. Swedek, Cupertino, CA (US); Jimin Zhang, San Jose, CA (US); Harry Q. Lee, Los Altos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 331 days.

(21) Appl. No.: 11/868,911

(22) Filed: Oct. 8, 2007

(65) Prior Publication Data

US 2008/0130000 A1  Jun. 5, 2008

Related U.S. Application Data

(60) Provisional application No. 60/868,673, filed on Dec. 5, 2006.

(51) Int. Cl.
 *G01B 9/08* (2006.01)
 *G01B 11/28* (2006.01)
(52) U.S. Cl. .................................. 356/630; 356/392
(58) Field of Classification Search ............... 356/630, 356/392
 See application file for complete search history.

(56) References Cited

U.S. PATENT DOCUMENTS

| | | | |
|---|---|---|---|
| 6,020,968 A | 2/2000 | Horie | |
| 6,153,116 A | 11/2000 | Yang et al. | |
| 6,271,047 B1 | 8/2001 | Ushio et al. | |
| 6,455,850 B1 * | 9/2002 | Coates et al. | 250/338.1 |
| 6,747,283 B1 | 6/2004 | Amartur | |
| 2002/0030826 A1 | 3/2002 | Chalmers et al. | |
| 2003/0087459 A1 | 5/2003 | Laursen et al. | |
| 2003/0197859 A1 | 10/2003 | Kubota et al. | |
| 2005/0026542 A1 | 2/2005 | Battal et al. | |

FOREIGN PATENT DOCUMENTS

JP  2003-264163  9/2003

OTHER PUBLICATIONS

Applied Materials, Inc., International Search Report and Written Opinion of the International Application No. PCT/US2007/086535 dated May 14, 2008, 16 pages.
Laursen, T. et al., "Multiprobe End-Point Detection for Precision Control of the Copper CMP Process", *Mat. Res. Soc. Symp. Proc.*, vol. 671 (2001), pp. M7.6.1-M7.6.6, XP009099778.

* cited by examiner

*Primary Examiner*—Michael P Stafira
(74) *Attorney, Agent, or Firm*—Fish & Richardson

(57) ABSTRACT

Methods of subtracting the copper contribution to spectra obtained from a substrate during chemical mechanical polishing are described.

23 Claims, 15 Drawing Sheets

DETERMINING COPPER CONCENTRATION IN SPECTRA

CROSS-REFERENCE TO RELATED APPLICATIONS

This application claims priority to U.S. Application Ser. No. 60/868,673, filed on Dec. 5, 2006, the disclosure of which is hereby incorporated by reference.

TECHNICAL FIELD

This invention relates to chemical mechanical polishing.

BACKGROUND

An integrated circuit is typically formed on a substrate by the sequential deposition of conductive, semiconductive, or insulative layers on a silicon wafer. One fabrication step involves depositing a filler layer over a non-planar surface and planarizing the filler layer. For certain applications, the filler layer is planarized until the top surface of a patterned layer is exposed. A conductive filler layer, for example, can be deposited on a patterned insulative layer to fill the trenches or holes in the insulative layer. After planarization, the portions of the conductive layer remaining between the raised pattern of the insulative layer form vias, plugs, and lines that provide conductive paths between thin film circuits on the substrate. For other applications, such as oxide polishing, the filler layer is planarized until a predetermined thickness is left over the non planar surface. In addition, planarization of the substrate surface is usually required for photolithography.

Chemical mechanical polishing (CMP) is one accepted method of planarization. This planarization method typically requires that the substrate be mounted on a carrier or polishing head. The exposed surface of the substrate is typically placed against a rotating polishing disk pad or belt pad. The polishing pad can be either a standard pad or a fixed abrasive pad. A standard pad has a durable roughened surface, whereas a fixed-abrasive pad has abrasive particles held in a containment media. The carrier head provides a controllable load on the substrate to push it against the polishing pad. A polishing slurry is typically supplied to the surface of the polishing pad. The polishing slurry includes at least one chemically reactive agent and, if used with a standard polishing pad, abrasive particles.

One problem in CMP is determining whether the polishing process is complete, i.e., whether a substrate layer has been planarized to a desired flatness or thickness, or when a desired amount of material has been removed. Overpolishing (removing too much) of a conductive layer or film leads to increased circuit resistance. On the other hand, underpolishing (removing too little) of a conductive layer leads to electrical shorting. Variations in the initial thickness of the substrate layer, the slurry composition, the polishing pad condition, the relative speed between the polishing pad and the substrate, and the load on the substrate can cause variations in the material removal rate. These variations cause variations in the time needed to reach the polishing endpoint. Therefore, the polishing endpoint cannot be determined merely as a function of polishing time.

SUMMARY

Methods for determining how much copper contributes to a measured spectra of reflected light are described. The method can use a normalized cross-correlation curve to determine the contribution from copper. This can provide a direct measure of the percentage of a signal that is due reflection from copper. The percentage of the spectra that is due to copper can then be subtracted from the measured spectra, resulting in only spectra resulting from the non-copper materials.

Advantages of the methods and systems described herein can include one or more of the following. Copper CMP typically is a multi-step process, where the last step includes thinning the dielectric material to a desired thickness. Although methods for selecting an endpoint of this last step exist, improved endpointing methods can allow for tighter control on polishing accuracy and substrate specifications. This can allow for flatter, more accurately polished substrates, greater reproducibility and higher production yield.

Broad wavelength spectra, e.g., white light spectra, has been found to be promising in endpoint determination, because of the amount of information that can be obtained with each spectrum. Also, white light spectra endpoint techniques allow for the detection of the barrier-to-oxide transition as well as provide a reliable way to remove a specified amount of oxide from the substrate. One difficulty with using white light spectra is that in regions of the substrate having exposed copper, the copper contributes to the spectra, when only the reflection from the dielectric material is desired. The reflection from copper is very strong and is not masked by the dielectric reflection. A further problem is that the amount of signal from copper in a given measured spectrum is random, because the copper structures on the substrate are irregular and non-homogenous. The strong reflection from copper coupled with the random amount of copper in any measured spectrum, hampers the ability to monitor barrier and oxide regions. Removing the copper signal from the measured spectrum can allow the endpoint method to work more reliably.

As used in the instant specification, the term substrate can include, for example, a product substrate (e.g., which includes multiple memory or processor dies), a test substrate, a bare substrate, and a gating substrate. The substrate can be at various stages of integrated circuit fabrication, e.g., it can include one or more deposited and/or patterned layers. The term substrate can include circular disks and rectangular sheets.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

A polishing system having an in-situ monitoring module can be used to monitor substrate polishing to obtain polishing data and determine a polishing endpoint on the fly or in real time. Such a polishing system and in-situ monitoring module are described in U.S. Patent Publication 2007-0224915, the disclosure of which is incorporated by reference. During polishing, the monitoring module obtains spectra reflected from the surface of a substrate. The spectra are then compared to a library to determine when an endpoint will be reached.

Figure 1:
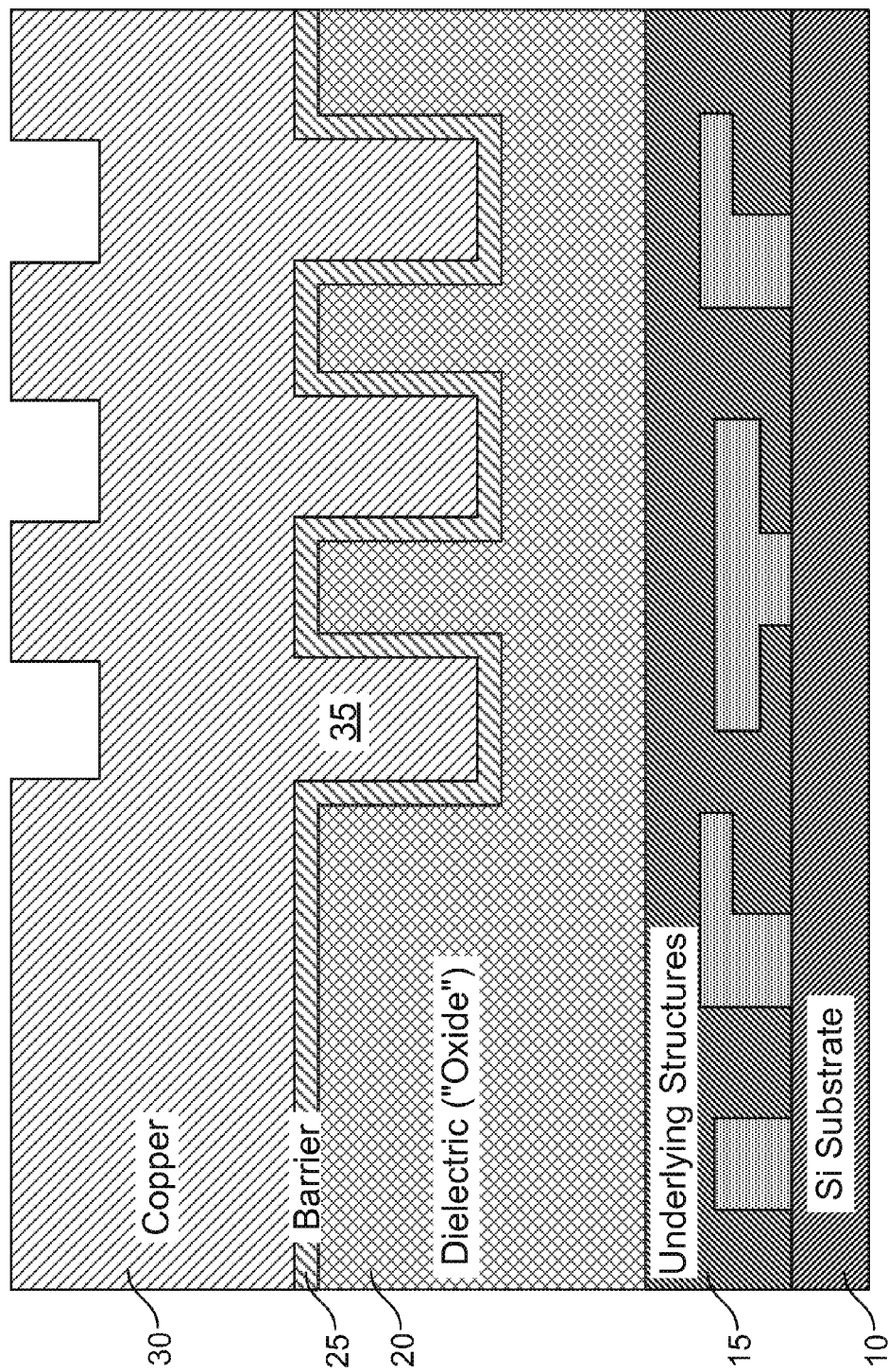
FIG. 1 shows a schematic of a cross-section of a portion of a substrate after copper deposition.
Figure 2:
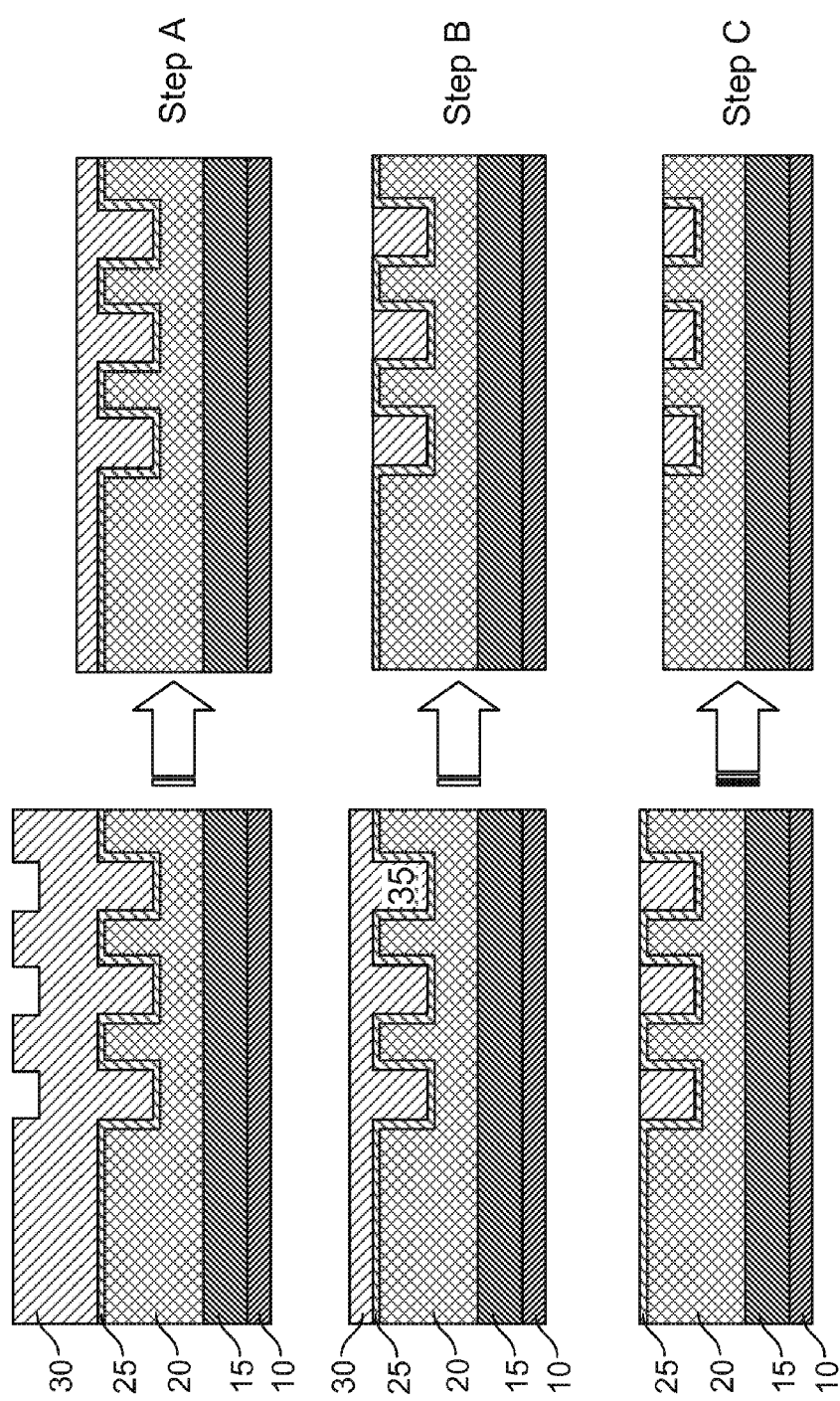
FIG. 2 shows schematics of the cross-sections of a portion of a substrate throughout a polishing process.

Referring to FIG. 1, a cross-section of a portion of the substrate after copper deposition shows a silicon substrate 10 with an underlying structure layer 15, a dielectric layer 20, a barrier layer 25 and a copper layer 30 thereon. Recesses 35 in the dielectric layer 20 that are filled with copper will form lines, pads and other conductive features. The substrate can be polished in one or more steps, as shown in FIG. 2. In the first polishing step, Step A, the copper layer 30 is planarized. In a second polishing step, Step B, the copper layer 30 is cleared from above the above the barrier layer 25 in the areas outside of the lines 35. In a third polishing step, Step C, the barrier layer 25 is removed from outside of the lines 35 and a portion of the dielectric layer 20 is removed. Additional polishing steps can occur. Further, the polishing steps can take place separately, such as on different platens of a polishing system, or two or more of the steps can be combined and take place on a single platen.

During Step C, the spectra based endpoint method can be used to determine the endpoint. A desired dielectric layer thickness is selected and during polishing, one of the methods for matching the spectra obtained in real time to spectra in a library of polishing spectra is used to determine the polishing endpoint. One potential problem lies in collecting the spectra from the substrate surface.

Figure 3:
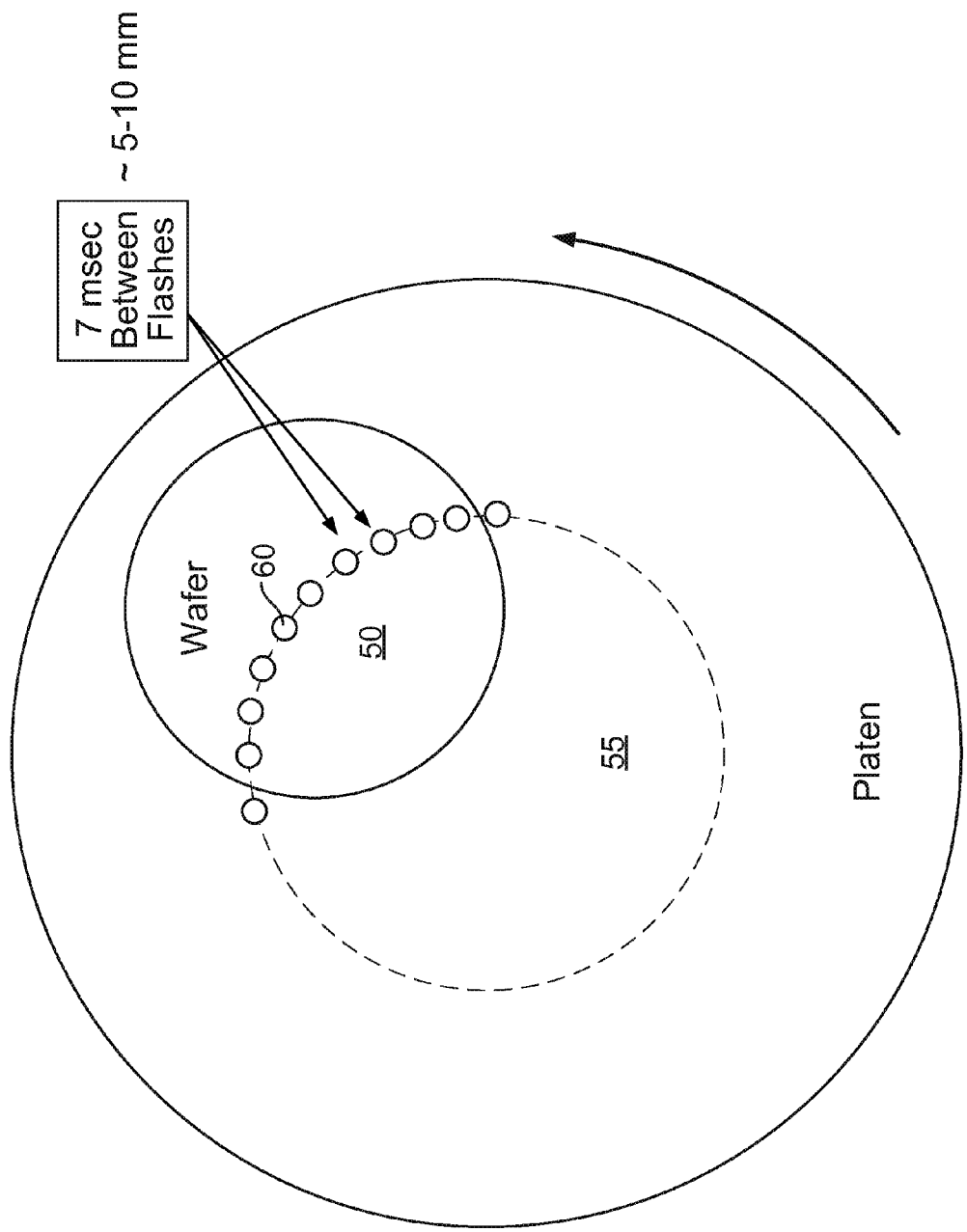
FIG. 3 is a schematic of a substrate on a platen.

Spectra is collected while the substrate is rotated and translated across a polishing surface. Referring to FIG. 3, some polishing systems rotate a polishing pad 55 on a platen to which the endpoint detection system is secured so that the sensor translates across the substrate 50. Spectra are obtained at locations 60 on the substrate 50 at intervals of a predetermined time and/or spacing, such as about 7 ms and 5-10 mm. Each spectrum is the result of light reflection from a measurement spot, which can be several mm across.

It is difficult to control the exact location of the portion of the substrate 50 from which the spectra will be retrieved. As shown in FIG. 2, the substrate 50 has, in addition to other features, both copper lines 35 and dielectric layer 20. Light reflected from the copper lines 35 has a more intense reflectance and a different spectral distribution than light reflected from the dielectric layer 20. In the endpoint determination method described in U.S. Patent Publication 2007-0224915, spectra from the dielectric areas are used to determine the endpoint. However, copper reflectance can cause strong, unwanted distortion in the spectra. Any reflection from copper can skew the spectra, which can make it unusable in its raw state for endpoint determination.

Figure 4:
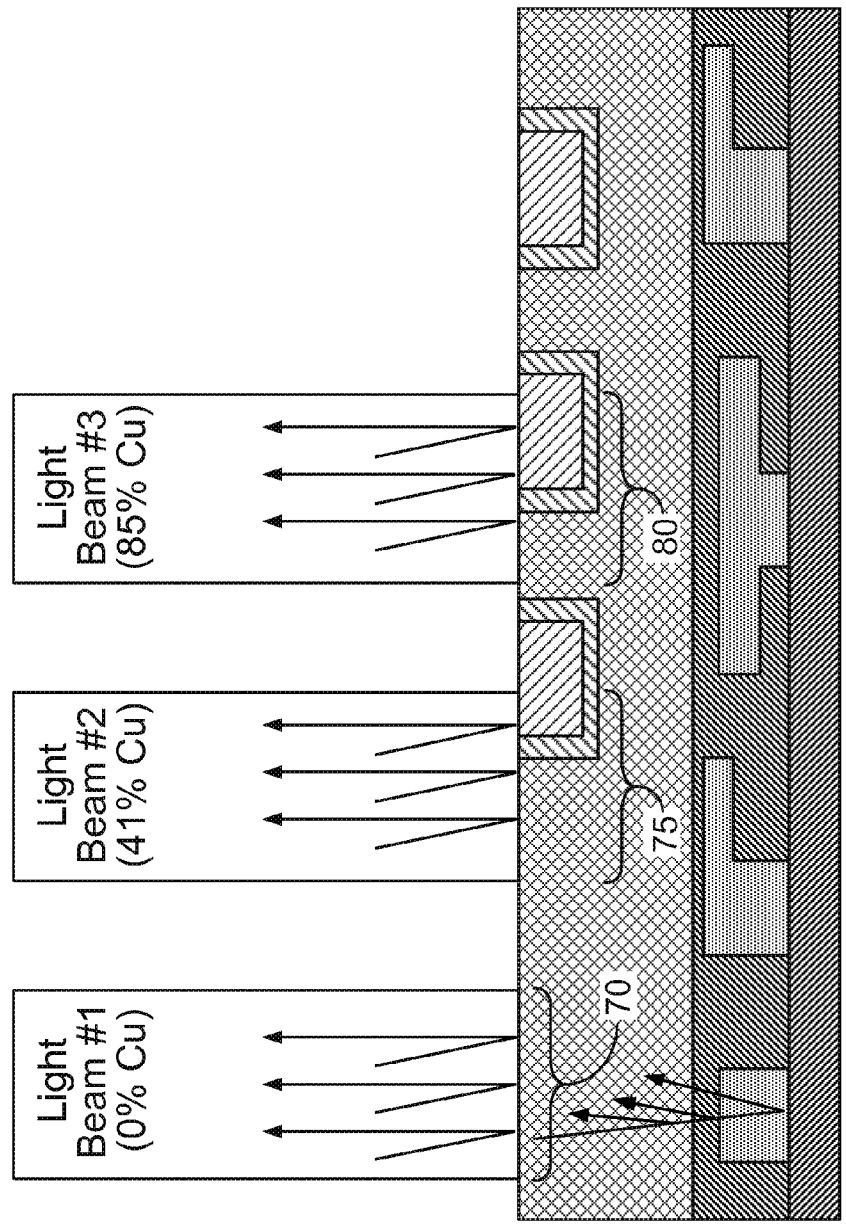
FIG. 4 is a schematic of light reflected from a portion of the surface of a substrate.

Referring to FIG. 4, in addition to skewing the spectra, the amount of copper reflectance varies widely and can be effectively random from measurement to measurement, because the location at which the spectra with respect to the copper lines and dielectric areas is obtained is not controllable. This can be due to, inter alia, lack of precision in motor encoders and substrate slippage in the carrier head, or the sweep path of the light beam across the substrate not passing over the same location on each die. One light beam may strike an area 70 with only dielectric, while other light beams may reflect off of areas 75, 80 of the substrate including both dielectric and copper (although shown as reflecting off only a single copper line, the measurement spot can include many lines or other copper features). And for areas 75, 80 that include dielectric and copper, the proportion of dielectric can vary. Feature density can vary from region to region on the substrate. Although some types of integrated circuits, such as memory, include large regions of regular metal features, other types of integrated circuits, such as processors, have non-uniform feature distribution. Thus, although the thickness of the dielectric layers in each of these areas 70, 75, 80, may be the same, the spectra will appear very different.

These spectra can be used, however, to determine the polishing endpoint. The spectra can be converted from their raw form, that is from how there are obtained, to a modified version which represent only the spectra that would be obtained if areas free from copper were used to obtain the spectra. The percentage of copper in the area from which each raw spectrum was obtained is determined. Then, the contribution from the copper to the spectrum is subtracted out.

Figure 5:
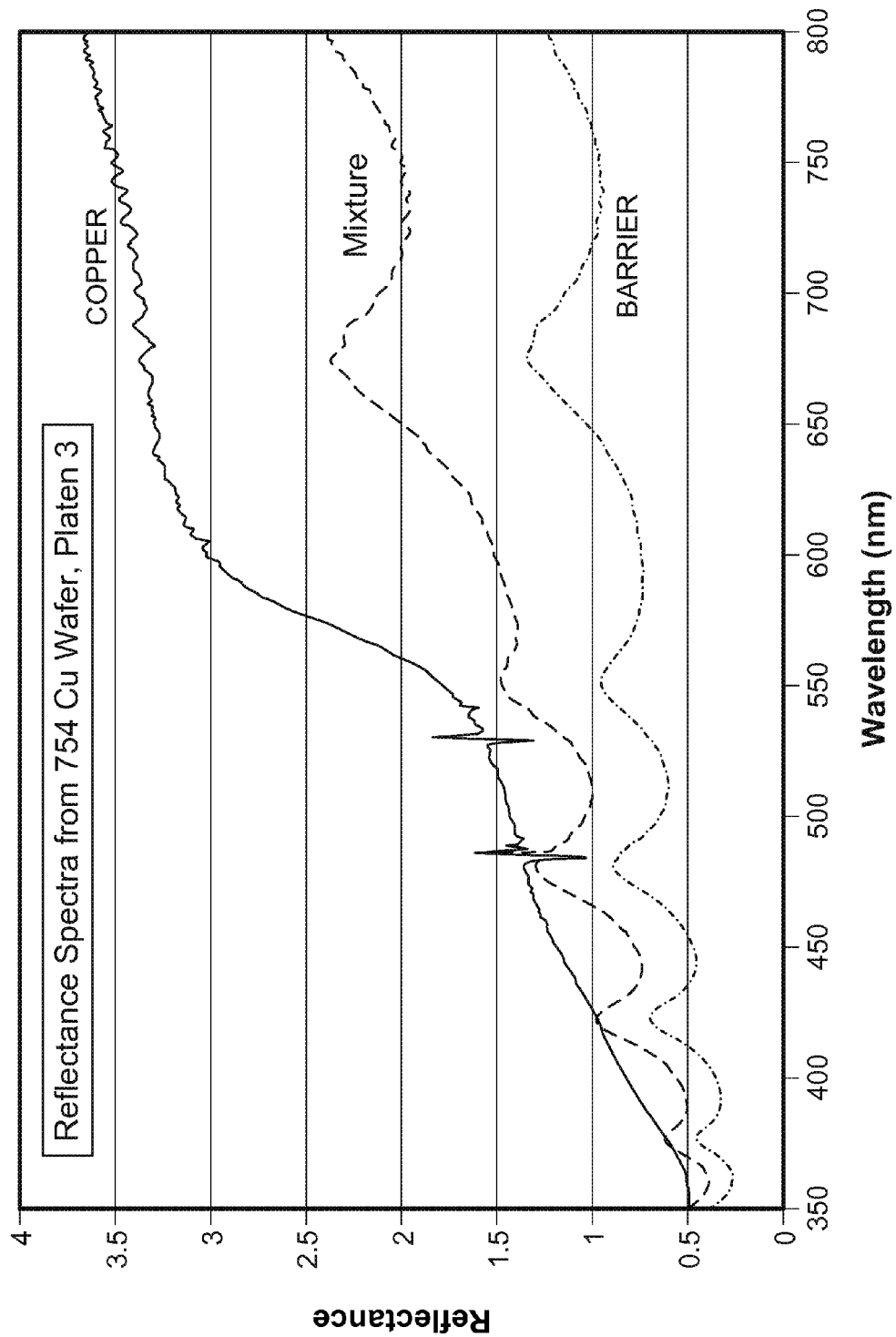
FIGS. 5, 6 and 7 show exemplary graphs of copper, dielectric and barrier material spectra.
Figure 6:
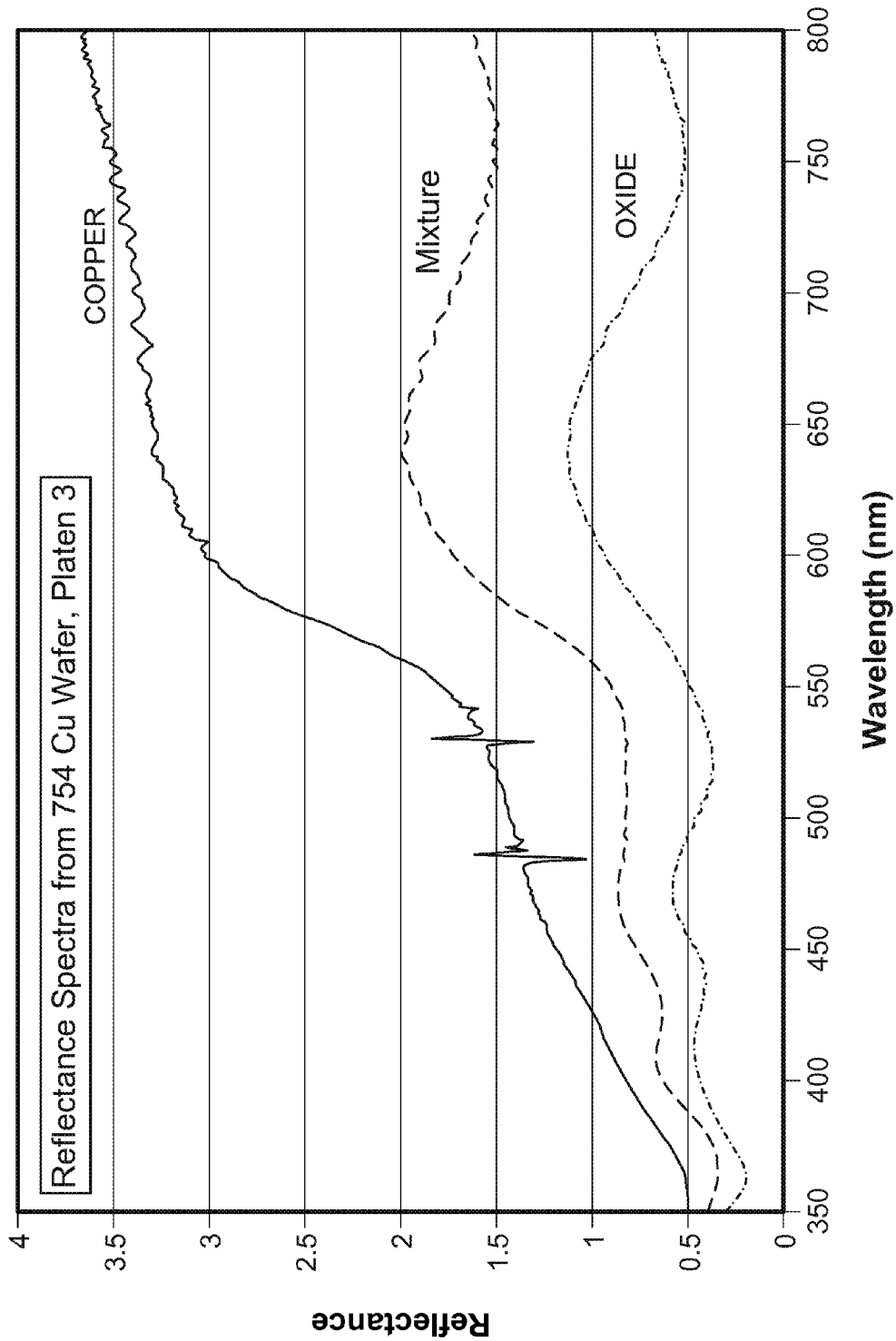
Figure 7:
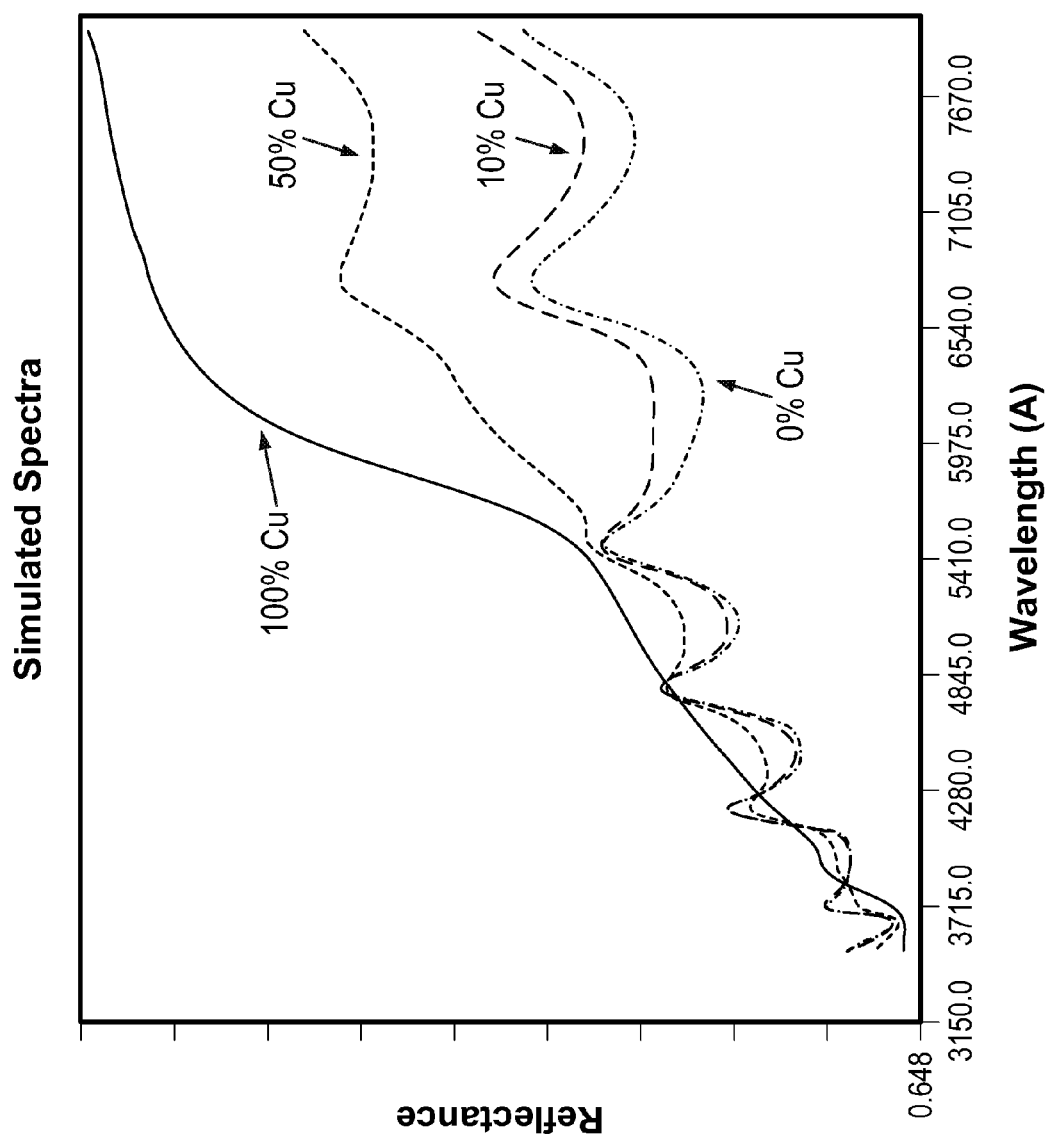

As shown in FIGS. 5, 6 and 7, the copper reflectance in a spectrum adds to the dielectric, or oxide, reflectance and to the barrier reflectance in a predictable way (assuming the percentage contribution from copper is known). Referring to FIG. 5, a spectrum for a pure copper layer, a spectrum for a pure barrier layer and a spectrum of a combination of copper and barrier are shown. The copper reflectance is higher than the barrier reflectance across all wavelengths. In FIG. 6, a similar phenomena is shown with oxide. A mixture of the copper and the oxide reflectance result in a spectrum with values between the two spectra. Referring to FIG. 7, as the percentage of copper decreases from 100% to 50%, 10% and 0%, the reflectance also decreases, for all wavelengths greater than 5410 Angstroms.

Figure 8:
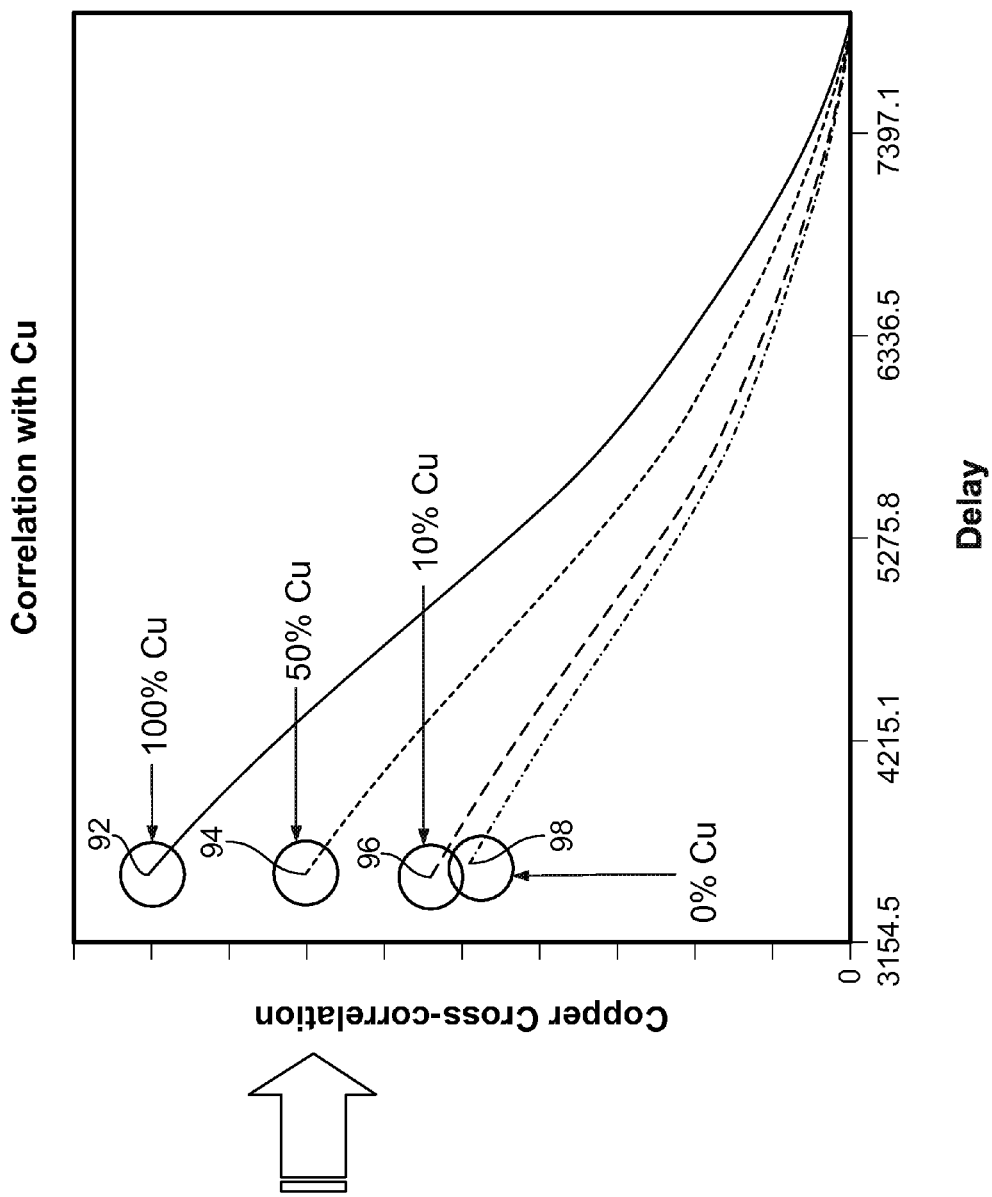
FIG. 8 shows correlation curves of spectra correlated with a 100% copper spectrum.

If each of the spectra are correlated with the pure or 100% copper spectrum and the result is normalized, at zero lag, the 10% copper spectrum normalizes to 0.1 and the 50% copper spectra normalizes to 0.5. Similar results are seen for the other percentages of copper. Referring to FIG. 8, a graph shows four spectra, for 0%, 10%, 50% and 100% copper correlated to the 100% copper spectrum at increasing lag ($\tau$ in the equation below). At the starting points 92, 94, 96, 98 of each spectra are the correlations of the spectra at zero lag, that is, when the curves are compared without shifting either curve along the x-axis. As the curve moves to the right along the graph, the lag increases and the correlation decreases.

To determine the copper concentration of a spectrum (i.e., the percentage contribution to the spectrum from copper, which is controlled by the percentage of the monitored surface area which is copper), the spectrum is correlated with the pure copper spectra at zero lag ($\tau$) using the following curve comparing equation $$f_{Cu} = \frac{Corr(\text{measured spectrum}) - Corr(\text{non Cu})}{Corr(\text{pure Cu}) - Corr(\text{non Cu})}$$

g(λ) represents one of the curves, such as the pure copper spectra, h(λ) represents the spectra that is measured, dλ indicates that the integral is carried out over λ the wavelength.

Next, the correlations of the measured spectrum at zero lag is normalized to obtain a concentration between 0 and 100%. This is achieved using the following equation $$Corr(g, h) = \int_{-\infty}^{\infty} g(\lambda + \tau) h(\lambda) d\lambda$$

where Corr(measured spectrum) is Corr(g,h) from the previous calculation, Corr(non Cu) is the value at starting point 98 and Corr(pure Cu) is the value at starting point 92 in FIG. 8. The constants Corr(non Cu) and Corr(pure Cu) are easily obtained empirically and are robust across different substrate patterns. The accuracy required for these constants is minimal, and even approximately correct values allow the copper subtraction method to greatly improve the signal-to-noise ratio of the endpoint trace.

Once the copper concentration has been determined, the copper contribution is subtracted form the measured spectrum. We assume a linear superposition of copper and non-copper spectra, weighted by the area fraction, or concentration, of each spectrum. The subtraction can be performed using the following equation $$M(\lambda) = (1 - f_{Cu}) \cdot O(\lambda) + f_{Cu} \cdot 30 C(\lambda)$$

where M(λ) is the measured spectrum, $f_{Cu}$ (from 0.0 to 1.0) is the fraction of copper, O(λ) is the non-copper spectrum and C(λ) is the copper spectrum. Solving for the non-copper spectrum results in the following equation $$O(\lambda) = \frac{[M(\lambda) - f_{Cu} \cdot C(\lambda)]}{(1 - f_{Cu})}$$

EXAMPLE

Two methods are available for determining the polishing endpoint using spectra obtained from white light reflections from a substrate during polishing. The first method can be called a differential method of determining the endpoint. The second method is referred to herein as a spectra index matching method of determining the endpoint. Either method is described further in U.S. Patent Publication 2007-0224915.

Figure 9:
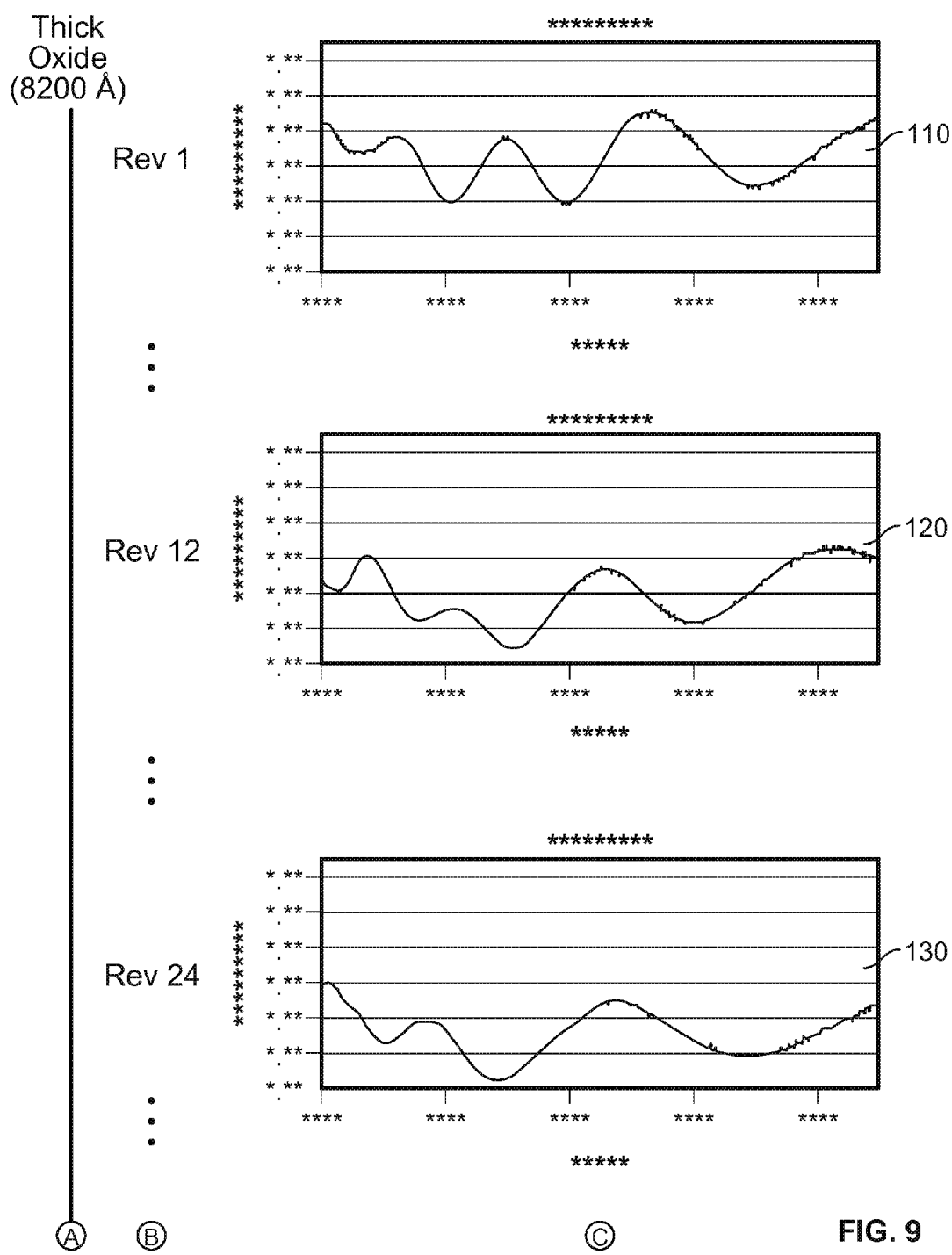
FIG. 9 shows exemplary spectra of dielectric material obtaining at various stages of a polishing process.
Figure 9:
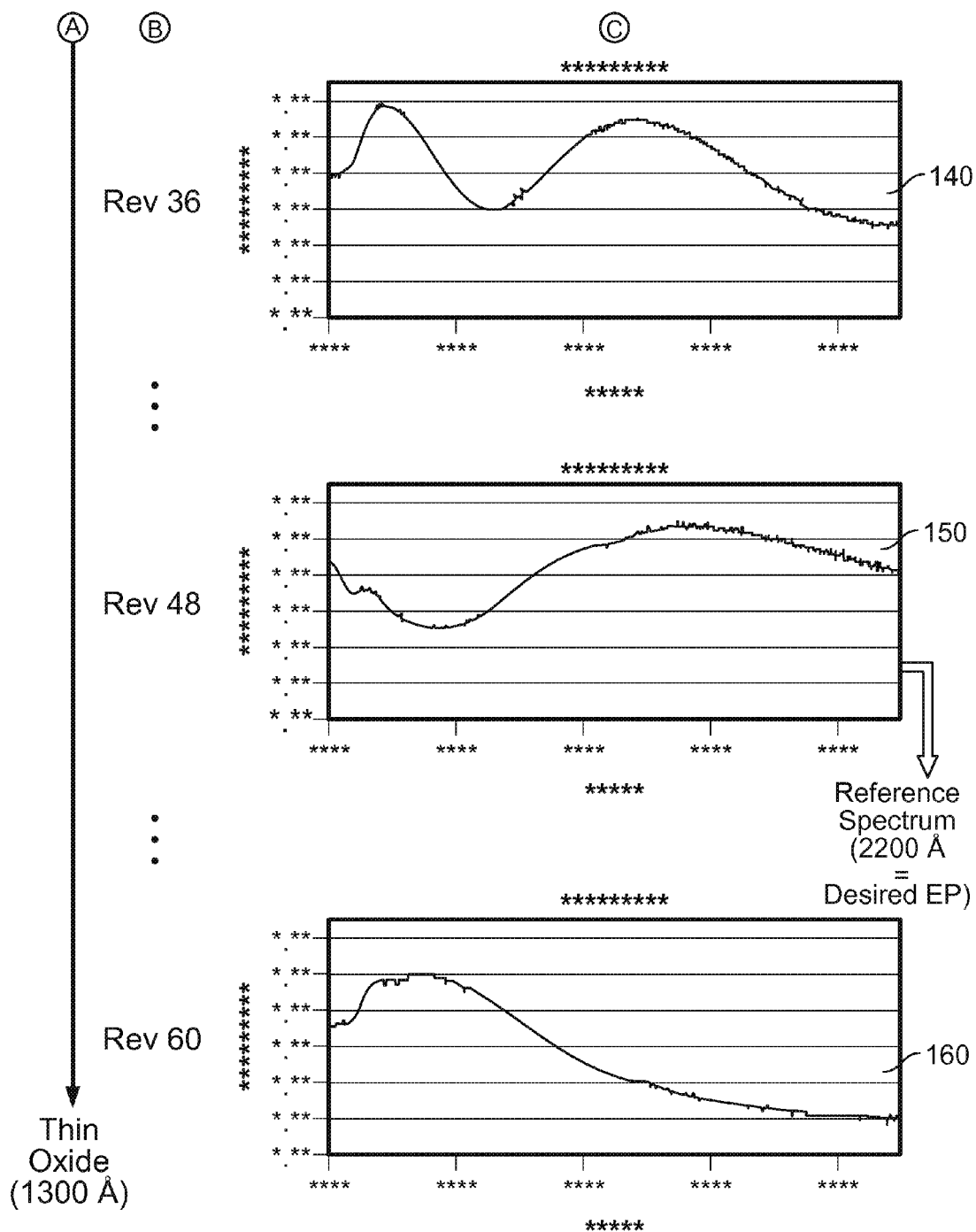

With either method, a library of polishing spectra are either obtained experimentally or theoretically determined. Referring to FIG. 9, the library can include spectra from a polishing sequence beginning with a spectrum 110 from a substrate having thick oxide layer—here, 8200 Å thick—and including spectra 120, 130, 140, 150, 160, throughout the polishing sequence to a point where the substrate has been overpolished—here, polished to 1300 Å thick. Only select spectra from the polishing sequence are shown, specifically, spectra at platen revolutions 1, 12, 24, 36, 48 and 60.

Spectra from other layers may also be obtained and stored in a library, such as spectra from a barrier layer. The barrier layer spectra can provide a way to determine when the barrier layer has been cleared.

For the differential method, a spectrum is selected corresponding to the desired endpoint oxide thickness for substrates undergoing the polishing operation. For example, if the desired oxide thickness is 2200 Å, which occurs at revolution 48, spectrum 150 is selected as the reference spectrum. Of course, other endpoints and other reference spectrum can be selected, as desired.

As a substrate is polished, polishing removes various materials from each layer, such as a copper, barrier material and oxide. The spectra that are obtained during polishing typically are reflected from one or more of these materials at any one time. Thus, in addition to using the method to determine oxide thickness, the method may be used to determine when a particular material has been removed from the substrate, such as the barrier layer.

For a substrate that is being polished, the spectra that are obtained are compared to the reference spectrum 150. To compare the spectra to the reference spectra, the differential between the two spectra is obtained as follows $$D = \sum_{\lambda} (R_m(\lambda) - R_r(\lambda))^2$$

where $R_m$ is the measure spectrum and $R_r$ is the reference spectrum. Simply put, the difference of the two spectra at each wavelength is determined, squared and summed.

Figure 10:
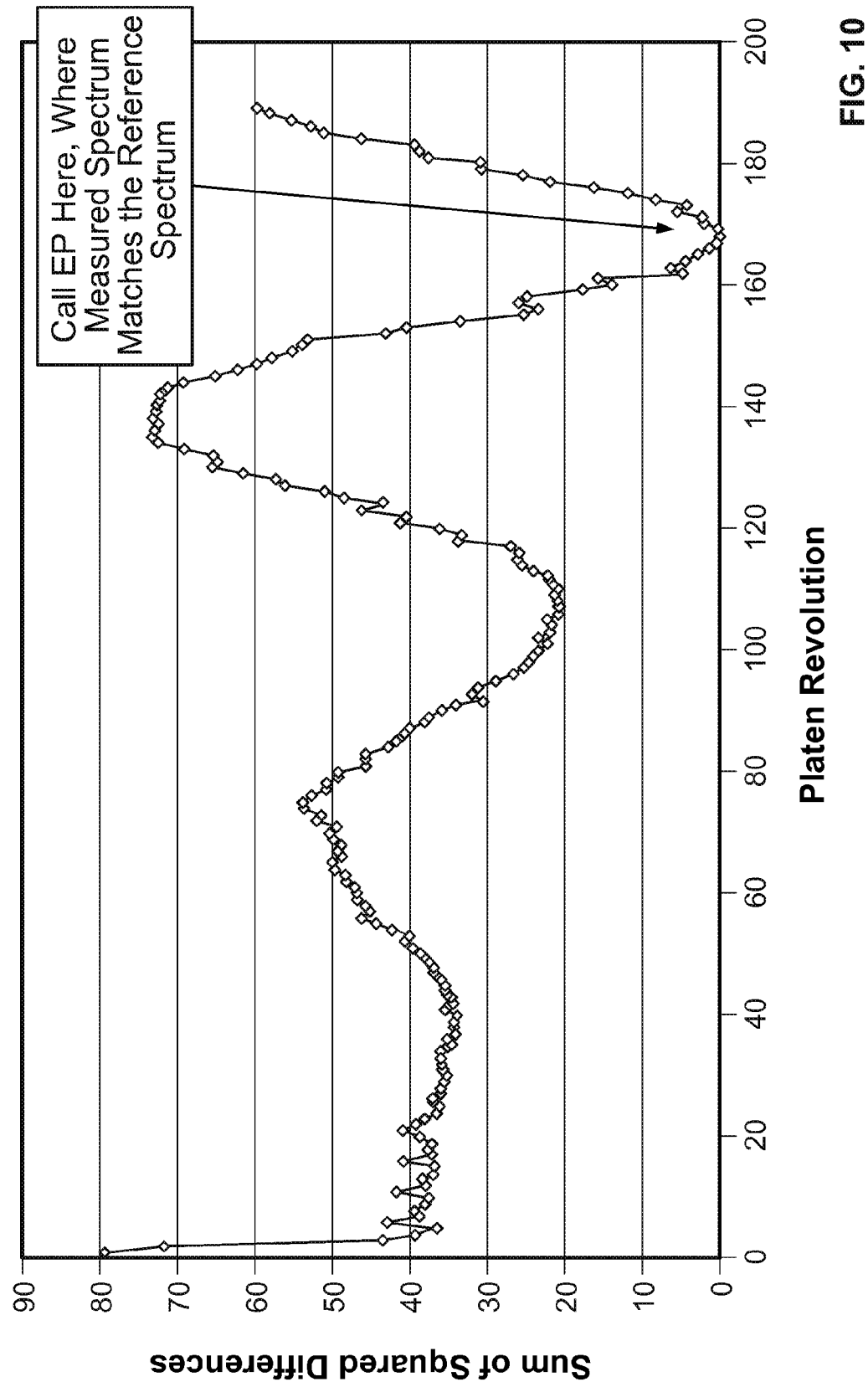
FIG. 10 shows a graph of the differential between measured spectra and a reference spectrum over a polishing process, used to determine a polishing endpoint.

Referring to FIG. 10, plotting the sum of the squared differences by platen revolutions results in a sinusoidal curve that approaches and retreats from zero. When the differential is closest to zero, the endpoint is called.

Figure 11:
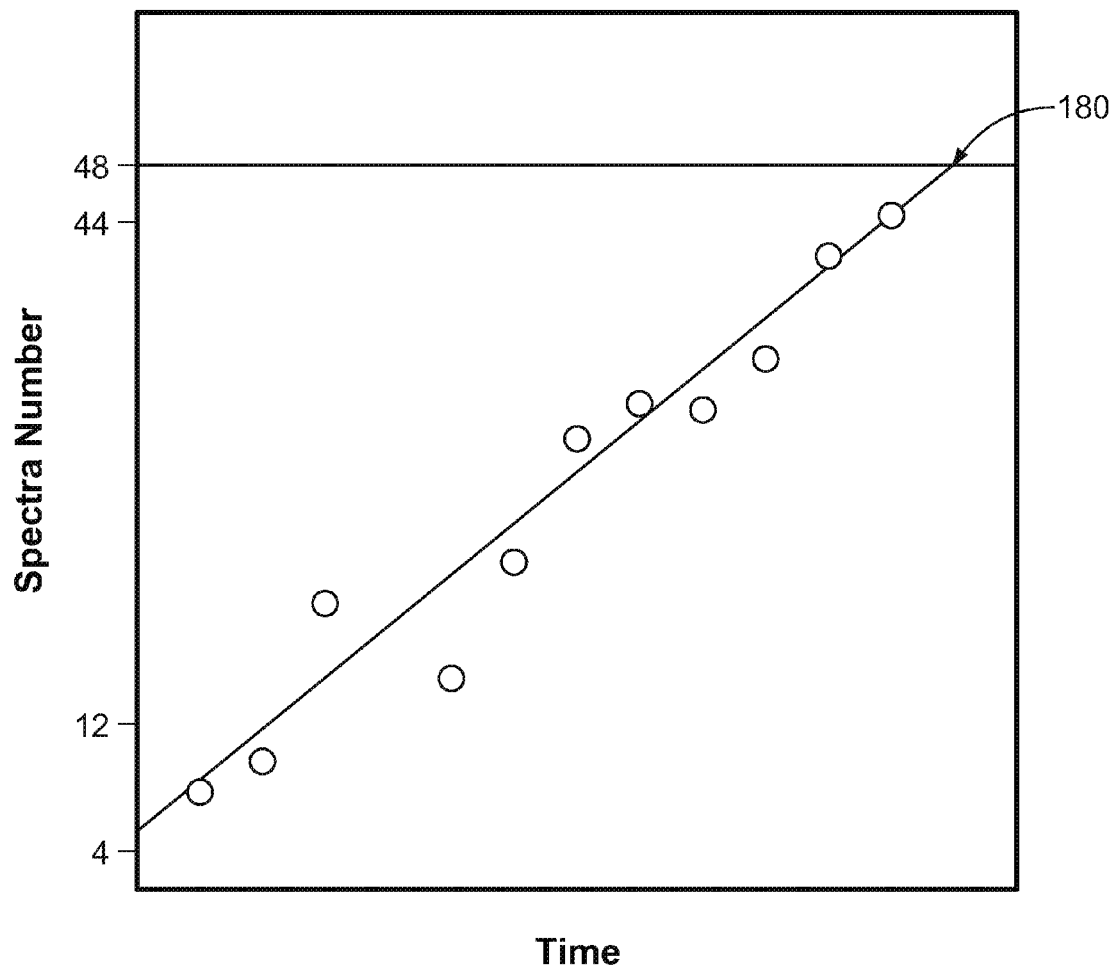
FIG. 11 shows a graph of the spectra matching method.

An alternative way of determining the endpoint, the spectra matching method, includes assigning a number to each spectra in the reference spectra. As each spectrum is obtained during polishing, the spectrum is matched to the library to determine the number of the spectrum in the library that the measured spectrum matches most closely. The matching numbers are plotted according to time, or platen rotation, and when the line intersects with the reference spectrum number, the endpoint is called. Referring to FIG. 11, an example of the spectra matching method shows a line fit to the results of the spectrum matching technique. The matched numbers are plotted according to time. When the line intersects with the reference spectra number, the endpoint is determined to occur at that time 180.

Figure 12:
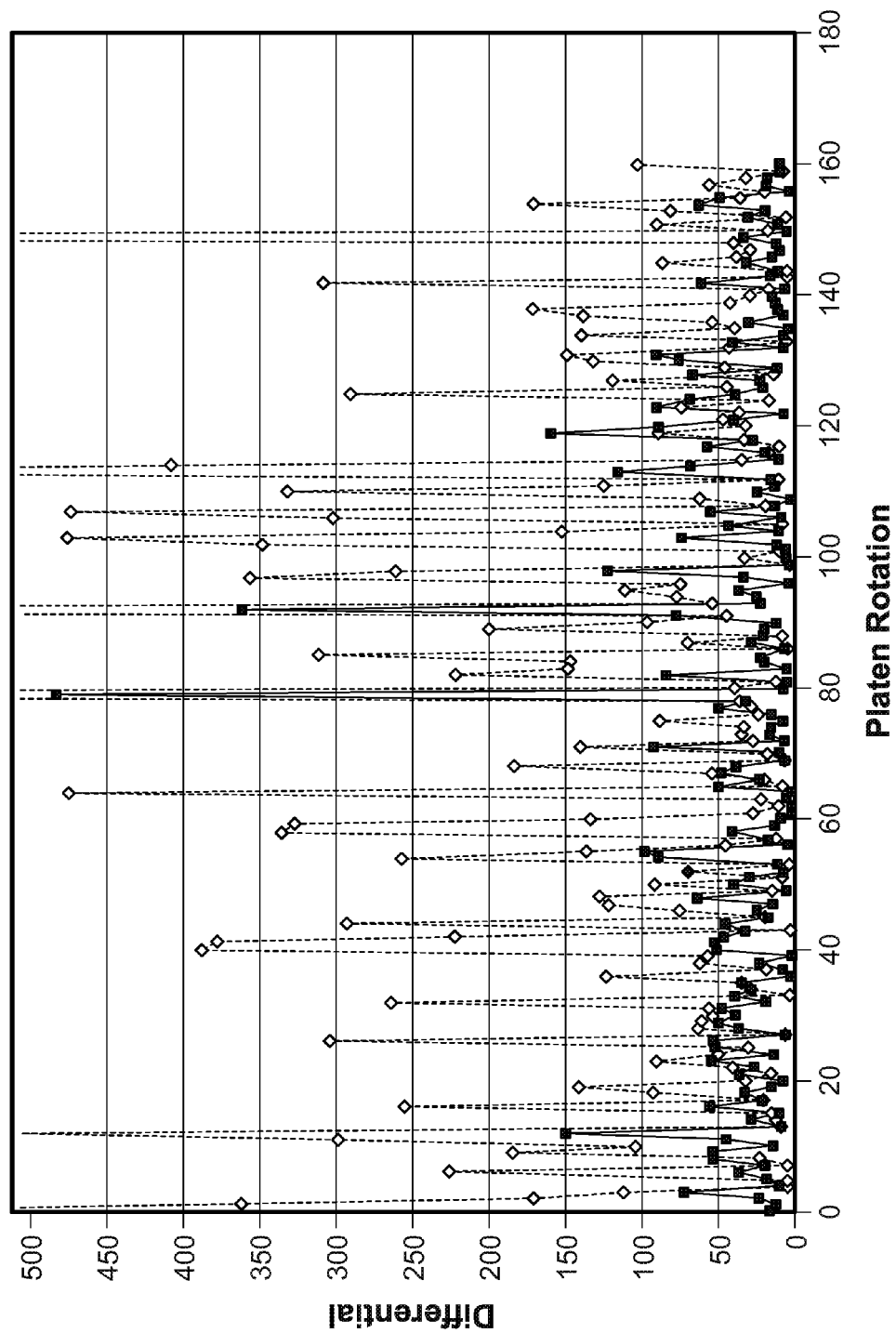
FIG. 12 shows a graph of the differential between measured spectra and a reference spectrum over a polishing process, before copper subtraction.

Referring back to the differential method of determining the endpoint, the differential plotted as shown in FIG. 10 typically is not obtainable from the raw spectra. This is due to the random addition of high reflectance from copper to each of the spectrum. Referring to FIG. 12, using raw spectra, which typically includes reflected light from both oxide and copper, can result in a differential plot that is difficult to use to determine the endpoint. FIG. 12 shows differential plots of two different substrates during polishing. Note the difference between the differential plots in FIGS. 10 and 12. The sinusoidal curve in FIG. 10 is easy to pick out while such curve in FIG. 12 is impossible to determine. The contribution, that is reflection, from the barrier layer, in these spectra after the point that the barrier layer has been polished away is generally negligible and is ignored.

Figure 13:
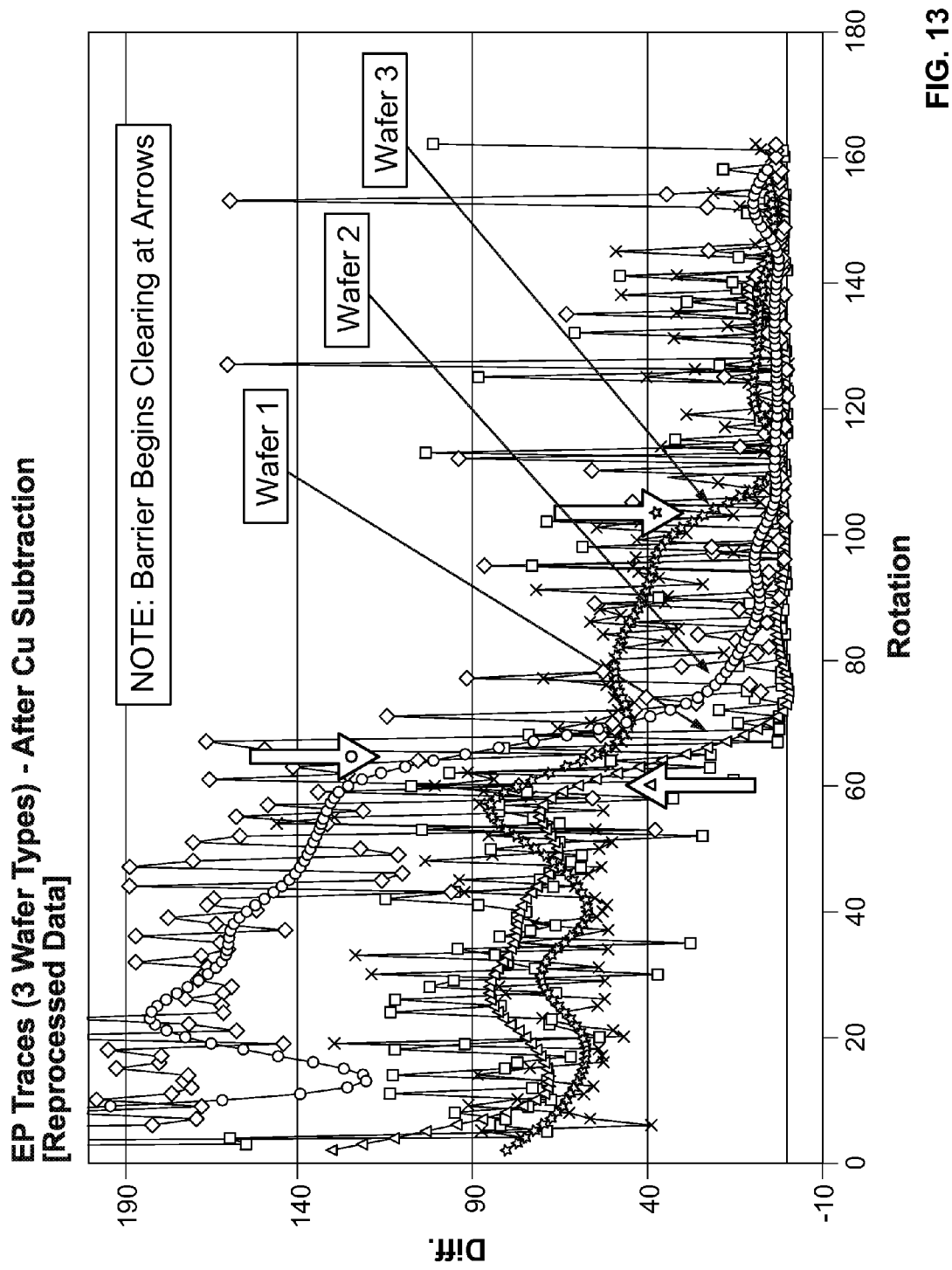
FIGS. 13 and 14 show graphs of the differential between measured spectra and a reference spectrum over a polishing process, after copper subtraction.
Figure 14:
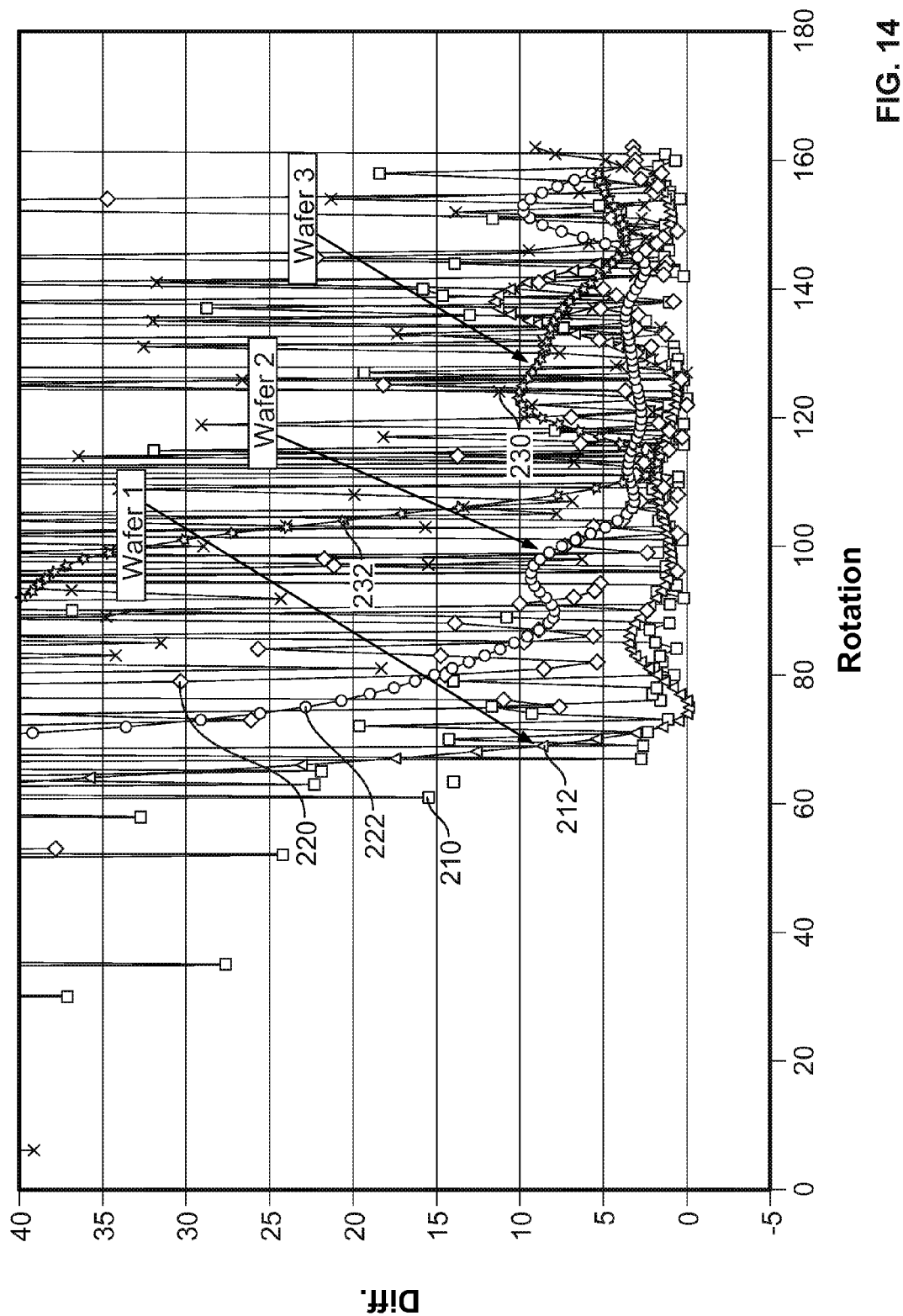

Referring to FIGS. 13 and 14, the differentials of three wafers after the copper contribution has been removed and their smoothed curves show how the endpoint can be determined. The differentials after copper subtraction 210, 220, 230 when plotted exhibit noise, but using curve smoothing techniques generates curves 212, 222, 232 that approach zero over time, or over platen rotations.

Although the method has been described in the context of copper, the method is applicable to other non-dielectric materials, e.g., metals, e.g., tungsten, that coat an underlying dielectric, e.g., a barrier layer, e.g., a nitride, e.g., a silicon or metal nitride.

Although the copper subtraction and endpoint techniques have been described with respect to the differential method of finding the endpoint, the method could similar be applied to the spectra matching method described herein.

The polishing tool on which the substrate is polished can include or can be in electrical communication with a processor that is able to determined the polishing endpoint using one of the methods described herein. Once the polishing endpoint has been determined, a controller uses the endpoint to signal the polisher to stop polishing.

Embodiments of the invention and all of the functional operations described in this specification can be implemented in digital electronic circuitry, or in computer software, firmware, or hardware, including the structural means disclosed in this specification and structural equivalents thereof, or in combinations of them. Embodiments of the invention can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment, A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

The above described polishing apparatus and methods can be applied in a variety of polishing systems. Either the polishing pad, or the carrier head, or both can move to provide relative motion between the polishing surface and the substrate. For example, the platen may orbit rather than rotate. The polishing pad can be a circular (or some other shape) pad secured to the platen. Some aspects of the endpoint detection system may be applicable to linear polishing systems, e.g., where the polishing pad is a continuous or a reel-to-reel belt that moves linearly. The polishing layer can be a standard (for example, polyurethane with or without fillers) polishing material, a soft material, or a fixed-abrasive material. Terms of relative positioning are used; it should be understood that the polishing surface and substrate can be held in a vertical orientation or some other orientation. Although subtracting out the contribution from copper in the spectra is described, reflection from other elements on the substrate can be removed in a similar manner, such as the barrier material. Accordingly, other embodiments are within the scope of the following claims.

What is claimed is:

1. A method of determining an amount of an area on a substrate that includes non-dielectric material, comprising:
    obtaining a measured spectrum of reflected light from a surface of the substrate;
    correlating the measured spectrum to a reference spectrum of reflected light from a non-dielectric material to obtain a correlation; and
    normalizing the correlation to obtain a concentration of the non-dielectric material in the area.

2. The method of claim 1, wherein the non-dielectric material is a metal.

3. The method of claim 2, wherein the non-dielectric material is copper.

4. The method of claim 1, wherein the surface includes regions of the non-dielectric material and regions of a dielectric material.

5. The method of claim 4, wherein the dielectric material is a barrier layer.

6. The method of claim 1, wherein correlating the measured spectrum to a spectrum of reflected light from a non-dielectric material includes correlating the measured spectrum to a spectrum of reflected light from an area having 100% of the non-dielectric material.

7. The method of claim 1, wherein obtaining the measured spectrum is performed while the substrate is undergoing polishing.

8. The method of claim 7, wherein obtaining the measured spectrum includes directing a light beam to the surface of the substrate and receiving reflections of the light beam.

9. The method of claim 8, wherein obtaining the measured spectrum is performed while the substrate is moving relative to the light beam.

10. A method of converting a spectrum obtained from an area on a substrate that includes dielectric material and non-dielectric material into a spectrum of only dielectric material, comprising:
    obtaining a measured spectrum of reflected light from a surface of the substrate;
    correlating the measured spectrum to a reference spectrum of reflected light from a non-dielectric material to obtain a correlation;
    normalizing the correlation to obtain a concentration of the non-dielectric material in the area; and
    subtracting a non-dielectric contribution to the measured spectrum from the measured spectrum.

11. The method of claim 10, wherein subtracting the non-dielectric contribution includes multiplying the concentration of the non-dielectric material by the reference spectrum to obtain a reduced reference spectrum, subtracting the reduced reference spectrum from the measured spectrum to obtain a dielectric component spectrum.

12. The method of claim 11, further comprising dividing the dielectric component spectrum by the concentration of the non-dielectric material to determine a dielectric material spectrum.

13. A method of determining a polishing endpoint, comprising:

during a polishing sequence, obtaining a measured spectrum of reflected light from an area on a surface of a substrate;

correlating the measured spectrum to a reference spectrum of reflected light from a non-dielectric material to obtain a correlation;

normalizing the correlation to obtain a concentration of the non-dielectric material in the area;

determining a dielectric material spectrum, including subtracting a non-dielectric contribution to the measured spectrum from the measured spectrum; and comparing the dielectric material spectrum to a reference spectrum to determine a polishing endpoint.

14. The method of claim 13, wherein obtaining a measured spectrum occurs while the substrate is moving relative to a sensor for receiving the measured spectrum.

15. The method of claim 13, wherein the substrate is a semiconductor substrate, the non-dielectric material is copper and the dielectric material is oxide.

16. The method of claim 13, further comprising stopping the polishing sequence at the polishing endpoint.

17. A computer program product, tangibly stored on machine readable medium, the product comprising instructions operable to cause a processor to:

receive a measured spectrum of reflected light from an area on a surface of the substrate;

correlate the measured spectrum to a reference spectrum of reflected light from a non-dielectric material to obtain a correlation; and normalize the correlation to obtain a concentration of the non-dielectric material in the area determine a dielectric material spectrum from the measured spectrum, first reference spectrum and concentration; and modify a polishing process based on a comparison of the dielectric material spectrum to a second reference spectrum.

18. The computer program product of claim 17, further comprising instructions to subtract a non-dielectric contribution to the measured spectrum from the measured spectrum.

19. The computer program product of claim 18, wherein instructions to subtract the non-dielectric contribution includes instructions to multiply the concentration of the non-dielectric material by the reference spectrum to obtain a reduced reference spectrum, and subtract the reduced reference spectrum from the measured spectrum to obtain a dielectric component spectrum.

20. The computer program product of claim 19, further comprising instructions to divide the dielectric component spectrum by the concentration of the non-dielectric material to determine a dielectric material spectrum.

21. The computer program product of claim 18, wherein subtracting the non-dielectric contribution to the measured spectrum from the measured spectrum determines a dielectric material spectrum, the product further comprising instructions to compare the dielectric material spectrum to a reference spectrum to determine a polishing endpoint.

22. The method of claim 13, wherein correlating the measured spectrum to a spectrum of reflected light from a non-dielectric material includes correlating the measured spectrum to a spectrum of reflected light from an area having 100% of the non-dielectric material.

23. The method of claim 22, further comprising stopping the polishing sequence at the polishing endpoint.

* * * * *

UNITED STATES PATENT AND TRADEMARK OFFICE
CERTIFICATE OF CORRECTION

| | | |
|---|---|---|
| PATENT NO. | : 7,768,659 B2 | Page 1 of 1 |
| APPLICATION NO. | : 11/868911 | |
| DATED | : August 3, 2010 | |
| INVENTOR(S) | : Dominic J. Benvegnu et al. | |

It is certified that error appears in the above-identified patent and that said Letters Patent is hereby corrected as shown below:

Col. 9, Claim 17, line 10, after "area" insert --;-- and begin a new line.

Signed and Sealed this

Thirtieth Day of November, 2010

David J. Kappos
*Director of the United States Patent and Trademark Office*